United States Patent [19]

Roloff et al.

[11] 4,322,432
[45] Mar. 30, 1982

[54] CYCLOPROPANECARBOXYLIC ACID ALKYNYL ESTERS, PROCESSES FOR PRODUCING THEM, AND THEIR USE AS PESTICIDES

[75] Inventors: Achim Roloff, Rheinfelden; Saleem Farooq, Ettingen, both of Switzerland

[73] Assignee: Ciba-Geigy Corporation, Ardsley, N.Y.

[21] Appl. No.: 214,296

[22] Filed: Dec. 8, 1980

[30] Foreign Application Priority Data

Dec. 14, 1979 [CH] Switzerland ............... 11094/79
Nov. 20, 1980 [CH] Switzerland ............... 8592/80

[51] Int. Cl.³ ............... A01N 43/02; A01N 37/00; C07C 69/74; C07D 333/24
[52] U.S. Cl. ............... 424/275; 424/305; 549/79; 560/124
[58] Field of Search ............... 549/79, 61, 62, 63, 549/64, 66, 68, 71; 560/124; 424/275, 305

[56] References Cited

U.S. PATENT DOCUMENTS 3,673,215 6/1972 Vollrath et al. ............... 549/79
4,003,945 1/1977 Kitamura et al. ............... 549/79

Primary Examiner—Alan Siegel
Attorney, Agent, or Firm—Frederick H. Rabin

[57] ABSTRACT

Cyclopropanecarboxylic acid alkynyl esters of the formula I

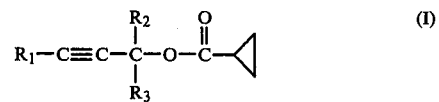

wherein $R_1$ is unsubstituted or substituted phenyl or thienyl, $R_2$ is hydrogen, alkyl having 1–6 C atoms, alkenyl having 2–6 C atoms, or phenyl or naphthyl which is unsubstituted or substituted by an alkyl or alkoxy group having 1–2 C atoms or by a halogen atom, and $R_3$ is hydrogen, alkyl having 1–6 C atoms or alkenyl having 2–6 C atoms, are suitable for combating various plant and animal pests, particularly insects, and members of the order Acarina. They can be obtained by reaction of corresponding alkynols with cyclopropanecarboxylic acid or with a reactive functional derivative thereof.

10 Claims, No Drawings

CYCLOPROPANECARBOXYLIC ACID ALKYNYL ESTERS, PROCESSES FOR PRODUCING THEM, AND THEIR USE AS PESTICIDES

The present invention relates to novel cyclopropanecarboxylic acid alkynyl esters, to processes for producing them, and to pesticidal compositions containing these cyclopropanecarboxylic acid alkynyl esters as active ingredients.

It is known that cyclopropanecarboxylic acid esters, for example cyclopropanecarboxylic acid alkyl and -phenyl esters, have an insecticidal and/or acaricidal action. Thus, for example, the cyclopropanecarboxylic acid esters described in the German Offenlegungsschrift No. 2,452,406 are suitable for combating mites, particularly red spider mites, some compounds also having an ovicidal action. The compounds mentioned in these publications have only a slight insecticidal action. The cycloalkanecarboxylic acid phenyl esters disclosed in the German Offenlegungsschrift No. 1,911,520 are used as, inter alia, acaricides and insecticides.

There have now been found novel cyclopropanecarboxylic acid alkynyl esters having an improved acaricidal and insecticidal action, especially an improved ovicidal action, against mites and insects.

The novel cyclopropanecarboxylic acid alkynyl esters correspond to the formula I

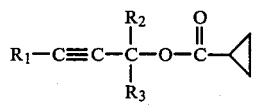

wherein $R_1$ is unsubstituted or substituted phenyl or thienyl, $R_2$ is hydrogen, alkyl having 1-6 C atoms, alkenyl having 2-6 C atoms, or phenyl or naphthyl which is unsubstituted or substituted by an alkyl or alkoxy group having 1-2 C atoms or by a halogen atom, and $R_3$ is hydrogen, alkyl having 1-6 C atoms or alkenyl having 2-6 C atoms.

When $R_1$ groups as defined are substituted, substituents are in particular halogen atoms, such as fluorine, bromine, chlorine or iodine, alkyl and alkoxy groups each having 1-5 C atoms, or trifluoromethyl, benzyl, hydroxyl, nitro, cyano, formyl or acetyl groups or alkoxycarbonyl groups having 1-5 C atoms in the alkoxy moiety. The $R_1$ groups can be mono- or polysubstituted by identical or different groups. Alkyl and alkoxy substituents as well as the alkoxy moieties in the alkoxycarbonyl groups can be straight-chain or branched-chain. They are in particular alkyl and alkoxy groups or alkoxycarbonyl groups having 1 or 2 C atoms in each of the alkyl or alkoxy moieties. The substituted phenyl group $R_1$ preferably has up to three, and particularly one or two, of the substituents mentioned above. Preferred substituents on phenyl group $R_1$ are chlorine, bromine and fluorine atoms, or methyl, ethyl, methoxy, ethoxy, nitro, —OH, trifluoromethyl, formyl, cyano, methoxycarbonyl and ethoxycarbonyl groups. The thienyl group $R_1$ is preferably unsubstituted.

Alkyl and alkenyl groups $R_2$ and $R_3$ can be straight-chain or branched-chain, and preferably each have at most 4 C atoms. The following may be mentioned as examples of such groups: the methyl, ethyl, n-propyl, isopropyl, n-, sec- and tert-butyl, n-pentyl, n-hexyl, vinyl, allyl and methallyl groups. When $R_2$ is substituted phenyl, it is in particular chlorophenyl, methyl- or methoxyphenyl. Naphthyl groups $R_2$ are preferably unsubstituted. Preferably, $R_2$ is hydrogen, alkyl or alkenyl having up to 4 C atoms or unsubstituted phenyl, and $R_3$ is hydrogen or alkyl having 1-4 C atoms.

Examples of compounds of the formula I which may be mentioned are: cyclopropanecarboxylic acid esters of 1-(3,4,5-trimethylphenyl)- or 1-(3,4,5-trichlorophenyl)-1-propyn-3-ol,
1-(2,3,5,6-tetrafluorophenyl)-1-propyn-3-ol,
1-(4-methoxy-2,3,5,6-tetrafluorophenyl)-1-propyn-3-ol,
1-(4-trifluoromethyl-2,3,5,6-tetrafluorophenyl)-1-propyn-3-ol,
1-(3,5-dimethoxyphenyl- or 3,5-diethoxyphenyl)-1-propyn-3-ol,
1-(2,4- and 3,5-dimethylphenyl)-1-propyn-3-ol or -3-methyl-1-butyn-3-ol,
1-(2-methoxy-4-formylphenyl)-1-propyn-3-ol,
1-(4-bromophenyl-phenyl)-3-methyl-1-butyn-3-ol,
1-(2-bromo-4,5-dimethoxyphenyl)-1-propyn-3-ol,
1-(2-nitro-4-bromophenyl)-1-propyn-3-ol,
1-(2-hydroxy-3-bromo-4-nitrophenyl)-1-propyn-3-ol,
1-(2-hydroxy-3-bromophenyl)-3-methyl-1-butyn-3-ol,
1-(4-bromo-3-methylphenyl)-3-methyl-1-butyn-3-ol,
1-(2-methyl-4-nitrophenyl)-1-propyn-3-ol,
1-(4-acetylphenyl)-3-methyl-1-butyn-3-ol,
1-(3- or 4-methylphenyl)-1-propyn-3-ol or -3-methyl-1-butyn-3-ol,
1-(4-ethylphenyl)-1-propyn-3-ol,
1-(2- or 4-methoxyphenyl)-1-propyn-3-ol,
1-(4-cyanophenyl)-3-phenyl-1-propyn-3-ol,
1-(4-cyanophenyl)-1-propyn-3-ol or -3-methyl-1-methyl-1-butyn-3-ol,
1-(2-hydroxyphenyl)-3-methyl-1-butyn-3-ol,
1-(4-hydroxyphenyl)-3-methyl-1-pentyn-4-en-3-ol,
1-(4-hydroxyphenyl)-1-propyn-3-ol,
1-(3-hydroxy-4-formylphenyl)-1-propyn-3-ol,
1-(2-methoxyphenyl)-1-butyn-3-ol,
1-(2-, 3- or 4-formylphenyl)-1-propyn-3-ol,
1-(2-, 3- or 4-trifluoromethylphenyl)-1-propyn-3-ol,
1-(2-, 3- or 4-chlorophenyl)-3-methyl-1-butyn-3-ol,
1-(4-methoxycarbonylphenyl- or 4-ethoxycarbonylphenyl)-1-propyn-3-ol,
1-(2-, 3- or 4-fluorophenyl)-1-propyn-3-ol,
1-(4-iodophenyl)-1-propyn-3-ol,
1-(2-hydroxy-3-iodo-5-nitrophenyl)-1-propyn-3-ol,
1-(2-, 3- or 4-nitrophenyl)-1-propyn-3-ol or -3-methyl-1-butyn-3-ol,
1-phenyl-1-propyn-3-ol, 1-phenyl-3-phenyl-1-butyn-3-ol,
1-phenyl-3-methyl-1-butyn-3-ol,
1-phenyl-3-phenyl-propyn-3-ol, 1-(4-benzyl-phenyl)-1-propyn-3-ol, and
1-(2-thienyl)-1-propyn-3-ol or -3-methyl-1-butyn-3-ol.

Preferred compounds of the formula I are those wherein $R_1$ is phenyl or thienyl which is unsubstituted or substituted by one or two halogen atoms, such as fluorine, chlorine or bromine, alkyl-, alkoxy- or alkoxycarbonyl groups having 1 to 2 C atoms in each of the alkyl or alkoxy moieties, formyl, hydroxyl, nitro, cyano and/or trifluoromethyl groups, $R_2$ is hydrogen, alkyl having 1-4 C atoms, particularly methyl, alkenyl having 2-4 C atoms, especially vinyl, or unsubstituted phenyl, and $R_3$ is hydrogen or alkyl having 1-4 C atoms, in particular methyl.

Particularly preferred compounds of the formula I are those wherein $R_1$ is phenyl, methylphenyl, methoxyphenyl, methoxycarbonylphenyl, chloro-, bromo- or fluorophenyl, cyanophenyl, formylphenyl, nitrophenyl, biphenyl, or 2-thienyl, $R_2$ is hydrogen, methyl or vinyl, and $R_3$ is hydrogen or methyl.

More especially preferred are compounds of the formula I wherein $R_1$ has the above-defined preferred meaning and is in particular 4-fluorophenyl or 2-thienyl, and $R_2$ and $R_3$ are hydrogen.

The compounds of the formula I can be produced by reacting a compound of the formula II $$R_1-C\equiv C-\underset{\underset{R_3}{|}}{\overset{\overset{R_2}{|}}{C}}-OH \qquad (II)$$

wherein $R_1$, $R_2$ and $R_3$ have the meanings defined under the formula I, in a manner known per se, with cyclopropanecarboxylic acid or with a reactive functional derivatives thereof, such as cyclopropanecarboxylic acid chloride or cyclopropanecarboxylic acid ester, such as cyclopropanecarboxylic acid alkyl ester having 1–6 C atoms in the alkyl moiety, or cyclopropanecarboxylic acid phenyl ester. Instead of the compounds of the formula II, also the corresponding alkali metal alcoholates can be reacted with cyclopropanecarboxylic acid chloride.

The compounds of the formula II are preferably reacted in the presence of an organic base and an inert organic solvent with cyclopropanecarboxylic acid chloride. The organic bases used are in particular tertiary amines, such as triethylamine or pyridine. Suitable inert organic solvents are for example aliphatic or aromatic hydrocarbons, such as n-pentane, n-hexane, benzene, toluene and xylenes, or aliphatic and cyclic ethers, such as dialkyl ether having 1–4 C atoms, and especially 1 or 2 C atoms, in each of the alkyl moieties, tetrahydrofuran, tetrahydropyrane and dioxane. The reaction temperatures are in general between about $-20°$ and $+150°$ C., preferably between about $+15°$ and $+100°$ C. The compounds of the formula I are obtained as a rule in the form of oils or crystals.

The cyclopropanecarboxylic acid and the reactive functional derivatives thereof are known. The compounds of the formula II are likewise known or can be produced by methods known per se, for example by reaction of compounds of the formula III $$R_2-CO-R_3 \qquad (III)$$

with acetylene derivatives of the formula IV $$HC\equiv C-R_1 \qquad (IV),$$

wherein $R_1$, $R_2$ and $R_3$ have the meanings given under the formula I, in the presence of suitable catalysts (cp. e.g. German Offenlegungsschriften Nos. 1,906,051 and 2,018,971, the French Patent Nos. 1,230,067 and 2,131,205 and U.S. Pat. Nos. 3,105,098 and 3,496,240).

The compounds of the formula II are produced, using a preferred process likewise known per se, by catalytically reacting a compound of the formula V $$R_1-X_1 \qquad (V)$$

with acetylene derivatives of the formula VI $$HC\equiv C-\underset{\underset{R_3}{|}}{\overset{\overset{R_2}{|}}{C}}-OH \qquad (VI)$$

wherein $R_1$, $R_2$ and $R_3$ have the meanings given under the formula I, and $X_1$ is a halogen atom, such as chlorine or iodine, particularly bromine. Suitable catalysts and solvents for the above reaction are described for example in: Tetrahedron Letters, 50, 4467–70 (1975); Journal of Organometallic Chemistry, 93, 253–257 and 259–263 (1973), the Italian Patent No. 1,006,879 and the U.S. Pat. No. 4,128,588. Preferred catalyst systems and solvents are those of the type mentioned in the last-mentioned U.S. patent specification.

The compounds of the formula I are suitable for combating various animal and plant pests, for example for combating representatives of the order Acarina of the families: Ioxididae, Argasidae, Tetranychidae and Dermanyssidae. The compounds of the formula I can be used successfully in particular for combating phytopathogenic mites, for example of the families Tetranychidae and Phytoptipalpidae (red spider mites), Tarsonemidae (tarsonemid mites) and Eriophydiae (gall mites). They are suitable particularly for combating the following genera of mites which infest cultivated crops of fruit and vegetables: *Tetranychus urticae, Tetranychus cinnabarinus, Panonychus ulmi, Broybia rubrioculus, Panonychus citri, Eriophyes pyri, Eriophyes ribis, Eriophyes vitis, Tarsomemus pallidus, Phyllocoptes vitis* and *Phyllocoptruta oleivora*.

The compounds of the formula I are suitable also for combating insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

The compounds of the formula I are suitable particularly for combating insects that damage plants, especially insects that damage plants by eating, in crops of ornamental plants and productive plants, in particular in cotton crops (for example against *Spodoptera littoralis* and *Heliothis virescens*), and in vegetable crops (for example against *Leptinotarsa decemlineata*). The compounds of the formula I are distinguished by a marked action against larval insect stages, especially against larval stages of eating insect pests. When the compounds of the formula I are taken up with the feed by adult insect stages, it can be confirmed in many cases, particularly in the case of Coleoptera, for example *Anthonomus grandis*, that a reduced oviposition and/or a decreased rate of emergence have resulted. The compounds of the formula I are characterised in particular by their ovicidal action against mites and insects. Finally, the active substances of the formula I also have a very effective action against flies, such as *Musca domestica*, and against mosquito larvae.

The acaricidal and insecticidal action of the compounds of the formula I can be substantially broadened and adapted to suit given circumstances by the addition of other insecticides and/or acaricides. Suitable additives are for example: organic phosphorus compounds, nitrophenols and derivatives thereof, formamidines, ureas, carbamates, pyrethrin-like compounds and chlorinated hydrocarbons.

Compounds of the formula I can be used on their own or together with suitable carriers and/or additives. Suitable carriers and additives can be solid or liquid and they correspond to the substances common in formulation practice, such as natural and regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions by customary methods of formulation which in application technology form part of common knowledge.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations: dusts, scattering agents, granules (coated granules, impregnated granules and homogeneous granules);

liquid preparations:
(a) water-dispersible concentrates of active substance: wettable powders, pastes and emulsions;
(b) solutions.

The content of active substance in the compositions described above is between 0.1 and 95%; it is to be mentioned in this respect that with application from an aeroplane, or from other suitable devices, concentrations of up to 99.5% or even the pure active substance can be used.

The active substances of the formula I can be formulated for example as follows (parts are by weight).

Dusts

The following substances are used to produce (a) a 5% dust and (b) a 2% dust:

(a)
  5 parts of active substance, and
  95 parts of talcum; and (b)
  2 parts of active substance,
  1 part of highly dispersed silicic acid, and
  97 parts of talcum.

The active substance is mixed and ground with the carriers.

Granulate

The following ingredients are used to produce a 5% granulate:
  5 parts of active substance,
  0.25 part of epoxidised vegetable oil,
  0.25 part of cetyl polyglycol ether,
  3.50 parts of polyethylene glycol, and
  91 parts of kaolin (particle size 0.3–0.8 mm).

The active substance is mixed with epoxidised vegetable oil and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)
  40 parts of active substance,
  5 parts of sodium lignin sulfonate,
  1 part of sodium dibutyl-naphthalene sulfonate, and
  54 parts of silicic acid;

(b)
  25 parts of active substance,
  4.5 parts of calcium lignin sulfonate,
  1.9 parts of Champagne chalk/hydroxyethyl cellulose mixture (1:1),
  1.5 parts of sodium dibutyl-naphthalene sulfonate,
  19.5 parts of silicic acid,
  19.5 parts of Champagne chalk, and
  28.1 parts of kaolin;

(c)
  25 parts of active substance,
  2.5 parts of isooctylphenoxy-polyoxyethyleneethanol,
  1.7 parts of Champagne chalk/hydroxyethyl cellulose mixture (1:1),
  8.3 parts of sodium aluminium silicate,
  16.5 parts of kieselguhr, and
  46 parts of kaolin; and (d)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:

(a)
  10 parts of active substance,
  3.4 parts of epoxidised vegetable oil,
  3.4 parts of a combination emulsifier consisting of fatty alcohol polyglycol ether and alkylarylsulfonate calcium salt,
  40 parts of dimethylformamide, and
  43.2 parts of xylene;

(b)
  25 parts of active substance,
  2.5 parts of epoxidised vegetable oil,
  10 parts of alkylarylsulfonate/fatty alcohol polyglycol ether mixture,
  5 parts of dimethylformamide, and
  57.5 parts of xylene; and (c)
  50 parts of active substance,
  4.2 parts of tributylphenol-polyglycol ether,
  5.8 parts of calcium-dodecylbenzenesulfonate,
  20 parts of cyclohexanone, and
  20 parts of xylene.

Emulsions of the required concentration can be prepared from these concentrates by dilution with water.

Sprays

The following constituents are used to produce (a) a 5% spray and (b) a 95% spray;

(a)
  5 parts of active substance,
  1 part of epichlorohydrin, and
  94 parts of ligroin (boiling limits 160°–190° C.);

(b)
95 parts of active substance, and
5 parts of epichlorohydrin.

The invention is further illustrated by the Examples which follow.

EXAMPLE 1

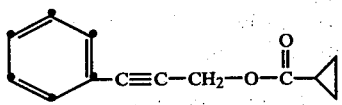

(a) A mixture of 0.7 g (1 mmol) of bis-triphenylphosphinepalladium dichloride and 0.38 g (2 mmols) of copper (I) iodide is added, with stirring, to 31.6 g (200 mmols) of bromobenzene, 16.8 g (300 mmols) of 1-propyn-3-ol and 300 ml of diethylamine. The reaction mixture is stirred in an argon atmosphere at room temperature (20°–25° C.), and within one hour the mixture heats up to about 30° C. A precipitate commences to occur, and after a reaction time of 6 hours, no further bromopyridine can be detected according to chromatographic analysis. 200 ml of diethyl ether are added to the reaction mixture and this is then filtered. The filtrate is washed with 200 ml of water, dried over magnesium sulfate, and concentrated by evaporation to leave a solid residue. Recrystallisation from diethyl ether yields 1-(phenyl)-propyn-3-ol. $^1$H-NMR Spectrum 100 MHz (CDCl$_3$, TMS) δ in ppm: 2.4(s); 4.5(s); 7.2–7.5(m) in the ratio of 1:2:5.

(b) 8.32 g (80 mmols) of cyclopropanecarboxylic acid chloride are dissolved in 30 ml of tetrahydrofuran, and 6.4 ml (80 mmols) of pyridine are added. There is then added dropwise to the mixture at 5° C. a solution of 10.7 g (80 mmols) of 1-(phenyl)-propyn-3-ol in 20 ml of tetrahydrofuran and 20 ml of pyridine. After completion of the addition, the reaction mixture is stirred for 2 hours at room temperature and then filtered. The filtrate is concentrated by evaporation, and purified through a column of 160 g of silica gel with ethyl acetate as eluant. The product is concentrated by evaporation to obtain 1-(phenyl)-1-propyn-3-yl-cyclopropanecarboxylic acid ester as a brownish-red oil.

IR Spectrum (film); 1740 cm$^{-1}$

2250 cm$^{-1}$ (—C≡C—).

$^1$H-NMR Spectrum 100 MHz (CDCl$_3$, TMS) δ in ppm: 0.8–1.2(m); 1.6–1.8(m); 4.9(s); 7.25–7.55(m) in the ratio 4:1:2:5.

EXAMPLE 2

(a) 1-(4-Formylphenyl)-1-propyn-3-ol-cyclopropanecarboxylic acid ester with use of 4-bromobenzaldehyde instead of bromonbenzene.

(b) 1-(4-Formylphenyl)-1-propyn-3-yl-cyclopropanecarboxylic acid ester (yield 80% of theory).

IR Spectrum (film): 1720, 1750 cm$^{-1}$ (—CO—).

$^1$H-NMR Spectrum, 100 MHz (CDCl$_3$, TMS) δ in ppm: 0.85–1.2(m); 1.6–1.8(m); 4.9(s); 7.6(d); 7.8(d); 10.1(s) in the ratio of 4:1:2:2:2:1.

EXAMPLE 3

(a) 1-Phenyl-3-methyl-1-butyn-3-ol (yield 86% of theory) with use of bromobenzene and 3-methyl-1-butyn-3-ol instead of 1-propyn-3-ol.

$^1$H-NMR Spectrum, 100 MHz (CDCl$_3$, TMS) δ in ppm: 1.6(s); 2.4(s); 7.2–7.4(m) in the ratio of 6:1:5.

(b) 1-Phenyl-3-methyl-1-butyn-3-yl-cyclopropanecarboxylic acid ester (yield 20% of theory).

IR Spectrum (film): 1740 cm$^{-1}$

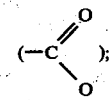

2250 cm$^{-1}$ (—C≡C—).

$^1$H-NMR Spectrum, 100 MHz (CDCl$_3$, TMS) δ in ppm: 0.8–1.2(m); 0.6–0.8(m); 0.8(s); 7.2–7.5(m) in the ratio of 4:1:6:5.

EXAMPLE 4

(a) 1-(4-Chlorophenyl)-propyn-3-ol; m.p. 78° C. (yield 80% of theory), with use of 4-chlorobromobenzene.

(b) 1-(4-Chlorophenyl)-1-propyn-3-yl-cyclopropanecarboxylic acid ester (yield 85% of theory).

IR Spectrum (film): 1740 cm$^{-1}$

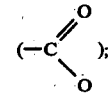

2250 cm$^{-1}$ (—C≡C—).

$^1$H-NMR Spectrum, 100 MHz (CDCl$_3$, TMS) δ in ppm: 0.8–1.2(m); 1.6–1.8(m); 4.9(s); 7.3–7.5(m) in the ratio of 4:1:2:4.

EXAMPLE 5

(a) 1-(4-Chlorophenyl)-3-methyl-1-butyn-3-ol (yield 87% of theory), with use of 4-chlorobromobenzene and 3-methyl-1-butyn-3-ol instead of 1-propyn-3-ol.

$^1$H-NMR Spectrum, 100 MHz (CDCl$_3$, TMS) δ in ppm: 1.6(s), 2.4(s); 7.2–7.4(m) in the ratio of 6:1:4.

(b) 1-(4-Chlorophenyl)-3-methyl-1-butyn-3-yl-cyclopropanecarboxylic acid ester (yield 32% of theory).

IR Spectrum (film): 1740 cm$^{-1}$

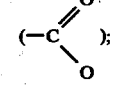

2250 cm$^{-1}$ (—C≡C—).

$^1$H-NMR Spectrum, 100 MHz (CDCl$_3$, TMS) δ in ppm: 0.8–1.2(m); 1.6–1.8(m); 1.85(s); 7.2–7.4(m) in the ratio of 4:1:6:4.

EXAMPLE 6

(a) 1-(4-Bromophenyl)-1-propyn-3-ol (yield 27% of theory) with the use of 1,4-dibromobenzene.

IR Spectrum (film): 2250 cm$^{-1}$ (—C≡C—); 3350 cm$^{-1}$ (—OH).

$^1$H-NMR Spectrum, 100 MHz (CDCl$_3$, TMS) δ in ppm: 2.15(t); 4.45(d); 7.2–7.5(m) in the ratio of 1:2:4.

(b) 1-(4-Bromophenyl)-1-propyn-3-yl-cyclopropanecarboxylic acid ester (yield 90% of theory).

IR Spectrum (film): 1745 cm$^{-1}$

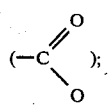

2250 cm$^{-1}$ (—C≡C—).

$^1$NMR Spectrum, 100 MHz (CDCl$_3$, TMS) δ in ppm: 0.8–1.2(m); 1.6–1.8(m); 4.95(s); 7.3–7.6(m) in the ratio of 4:1:2:4.

EXAMPLE 7

(a) 1-(4-Cyanophenyl)-1-propyn-3-ol; m.p. 88°–90° C. (yield 70% of theory), with use of 4-bromobenzonitrile.

(b) 1-(4-Cyanophenyl)-1-propyn-3-yl-cyclopropanecarboxylic acid ester (yield 88% of theory).

IR Spectrum (film): 1745 cm$^{-1}$

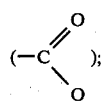

2230 cm$^{-1}$ (—C≡N; —C≡C—).

$^1$N NMR Spectrum, 100 MHz (CDCl$_3$, TMS) δ in ppm: 0.9–1.2(m); 1.65–1.85(m); 4.85(s); 7.55(m) in the ratio of 4:1:2:4.

EXAMPLE 8

(a) 1-(2-Trifluoromethylphenyl)-1-propyn-3-ol (87% of theory), with the use of 2-trifluoromethyl-bromobenzene.

$^1$H-NMR Spectrum, 100 MHz (CDCl$_3$, TMS) δ in ppm: 1.6(s); 2.3(s); 7.2–7.7(m) in the ratio of 6:1:4.

(b) 1-(2-Trifluoromethylphenyl)-1-propyn-3-yl-cyclopropanecarboxylic acid ester (yield 21% of theory).

IR Spectrum (film): 1740 cm$^{-1}$

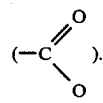

$^1$H-NMR Spectrum, 100 MHz (CDCl$_3$, TMS) δ in ppm: 0.8–1.2(m); 1.6–1.8(m); 1.9(s); 7.3–7.8(m) in the ratio of 4:1:6:4.

EXAMPLE 9

(a) 1-(4-Cyanophenyl)-3-methyl-1-butyn-3-ol) 97% of theory), with use of 4-bromobenzonitrile and 3-methyl-1-butyn-3-ol instead of 1-propyn-3-ol.

$^1$NMR Spectrum, 100 MHz (CDCl$_3$, TMS) δ in ppm: 1.6(s); 2.5(s); 7.4–7.7(m) in the ratio of 6:1:4.

(b) 1-(4-Cyanophenyl)-3-methyl-1-butyn-3-yl-cyclopropanecarboxylic acid ester (yield 30% of theory).

IR Spectrum (KBr): 1740 cm$^{-1}$

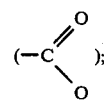

2280 cm$^{-1}$ (—C≡N; —C≡C—).

$^1$H-NMR Spectrum, 100 MHz (CDCl$_3$, TMS) δ in ppm: 0.8–1.2(m); 1.6–1.8(m); 1.9(s); 7.5–7.7(m) in the ratio of 4:1:6:4.

EXAMPLE 10

(a) 1-(4-Methoxyphenyl)-1-propyn-3-ol (yield 60.9% of theory), with use of 4-methoxybromobenzene.

$^1$H-NMR Spectrum, 100 MHz (CDCl$_3$, TMS) δ in ppm: 2.3(s); 3.7(s); 4.45(s); 6.7–6.9(m); 7.2–7.4(m) in the ratio of 1:3:2:2:2.

(b) 1-(4-Methoxyphenyl)-1-propyn-3-yl-cyclopropanecarboxylic acid ester (yield 58% of theory).

IR Spectrum (KBr): 1740 cm$^{-1}$

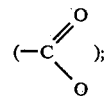

2300 cm$^{-1}$ (—C≡C—).

$^1$H-NMR Spectrum, 100 MHz (CDCl$_3$, TMS) δ in ppm: 0.8–1.2(m); 1.6–1.8(m); 3.8(s); 4.9(s); 6.75(m); 7.35(m) in the ratio of 4:1:3:2:2:2.

EXAMPLE 11

(a) 1-(4-Methylphenyl)-1-propyn-3-ol (81% of theory), with use of 4-bromotoluene.

$^1$H-NMR Spectrum, 100 MHz (CDCl$_3$, TMS) δ in ppm: 2.25(s); 3.0(s); 4.4(s); 7.0(d); 7.3(d) in the ratio of 3:1:2:2:2.

(b) 1-(4-Methylphenyl)-1-propyn-3-yl-cyclopropanecarboxylic acid ester (yield 94% of theory).

IR Spectrum (film): 1730 cm$^{-1}$

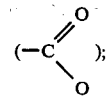

2250 cm$^{-1}$ (—C≡C—).

$^1$H-NMR Spectrum, 100 MHz (CDCl$_3$, TMS) δ in ppm: 0.8–1.2(m); 1.6–1.8(m); 2.3(s); 4.9(s); 7.05(d); 7.3(d) in the ratio of 4:1:3:2:2:2.

EXAMPLE 12

(a) 1-(2-Nitrophenyl)-1-propyn-3-ol (90% of theory), with use of 2-nitrobromobenzene).

$^1$H-NMR Spectrum, 100 MHz (CDCl$_3$, TMS) δ in ppm: 2.95(s); 4.5(s); 7.2–7.5(m); 7.8–8.0(m) in the ratio of 1:2:3:1.

(b) 1-(2-Nitrophenyl)-1-propyn-3-yl-cyclopropanecarboxylic acic ester (yield 50% of theory).

IR Spectrum (film): 1740 cm$^{-1}$

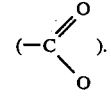

$^1$H-NMR Spectrum, 100 MHz, (CDCl$_3$, TMS) δ in ppm: 0.8–1.2(m); 1.6–1.8(m); 4.95(s); 7.4–7.7(m); 8.0–8.1(m) in the ratio of 4:1:2:3:1.

EXAMPLE 13

(a) 1-(2-Chlorophenyl)-1-propyn-3-ol (75% of theory), with use of 2-chlorobromobenzene.

$^1$H-NMR Spectrum, 100 MHz (CDCl$_3$, TMS) δ in ppm: 2.2(s); 4.5(s); 7.0–7.6(m) in the ratio of 1:2:4.

(b) 1-(2-Chlorophenyl)-1-propyn-3-yl-cyclopropanecarboxylic acid ester (yield 69% of theory).

IR Spectrum (film): 1745 cm$^{-1}$

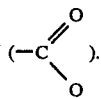

¹H-NMR Spectrum, 100 MHz (CDCl₃, TMS) δ in ppm: 0.8–1.2(m); 1.6–1.8(m); 4.95(s); 7.1–7.7(m) in the ratio of 4:1:2:4.

EXAMPLE 14

(a) 1-(4-Fluorophenyl)-1-propyn-3-ol (33% of theory), with use of 4-fluorobromobenzene.

¹NMR Spectrum, 100 MHz (CDCl₃, TMS) δ in ppm: 2.3(s); 4.45(s); 6.8–7.1(m); 7.3–7.5(m) in the ratio of 1:2:2:2.

(b) 1-(4-Fluorophenyl)-1-propyn-3-yl-cyclopropanecarboxylic acid ester (yield 87% of theory).

IR Spectrum (film): 1740 cm⁻¹

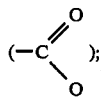

2250 cm⁻¹ (—C≡C—).

¹H-NMR Spectrum, 100 MHz (CDCl₃, TMS) δ in ppm: 0.8–1.2(m); 1.6–1.8(m); 4.95(s); 6.9–7.1(m); 7.3–7.6(m) in the ratio of 4:1:2:2:2.

EXAMPLE 15

(a) 1-(4-Methoxycarbonylphenyl)-1-propyn-3-ol; m.p. 81°–83° C. (yield 92% of theory), with use of 4-bromobenzoic acid methyl ester.

(b) 1-(4-Methoxycarbonylphenyl)-1-propyn-3-yl-cyclopropanecarboxylic acid ester (yield 90% of theory).

IR Spectrum (KBr): 1740 cm⁻¹

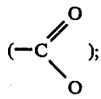

¹H-NMR Spectrum, 100 MHz (CDCl₃, TMS) δ in ppm: 0.8–1.2(m); 1.6–1.8(m); 3.95(s); 4.95(s); 7.55(d); 8.0(d) in the ratio of 4:1:3:2:2:2.

EXAMPLE 16

(a) 1-(2-Nitrophenyl)-1-butyn-3-ol (yield 99% of theory), with use of 2-bromonitrobenzene and 1-butyn-3-ol instead of 1-propyn-3-ol.

¹H-NMR Spectrum, 100 MHz (CDCl₃, TMS) δ in ppm: 1.6(d); 2.7(s); 4.8(q); 7.3–7.6(m); 7.9–8.1(m) in the ratio of 3:1:1:3:1.

(b) 1-(2-Nitrophenyl)-1-butyn-3-yl-cyclopropanecarboxylic acid ester (yield 93% of theory).

IR Spectrum (film): 1740 cm⁻¹

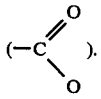

¹H-NMR Spectrum, 100 MHz (CDCl₃, TMS) δ in ppm: 0.8–1.2(m); 1.6–1.8(m); 1.75(d); 5.7(q); 7.3–7.7(m); 8.0–8.2(m) in the ratio of 4:1:3:1:3:1.

EXAMPLE 17

(a) 1-(3-Chlorophenyl)-1-propyn-3-ol (yield 80% of theory), with use of 3-bromochlorobenzene.

¹H-NMR Spectrum, 100 MHz (CDCl₃, TMS) δ in ppm: 2.2–2.4(s); 4.45(s); 7.2–7.5(m) in the ratio of 1:2:4.

(b) 1-(3-Chlorophenyl)-1-propyn-3-yl-cyclopropanecarboxylic acid ester (yield 60% of theory).

IR Spectrum (film): 1740 cm⁻¹

¹H-NMR Spectrum, 100 MHz (CDCl₃, TMS) δ in ppm: 0.8–1.2(m); 1.6–1.8(m); 4.95(s); 7.2–7.5(m) in the ratio of 4:1:2:4.

EXAMPLE 18

(a) 1-(2-Thienyl)-1-propyn-3-ol (yield 70% of theory), with use of 2-bromothiophene.

¹H-NMR Spectrum, 100 MHz (CDCl₃, TMS) δ in ppm: 2.2–2.3(s); 4.5(s); 6.9(m); 7.25(m) in the ratio of 1:2:1:2.

(b) 1-(2-Thienyl)-1-propyn-3-yl-cyclopropanecarboxylic acid ester (yield 70% of theory).

IR Spectrum (film): 1740 cm⁻¹

2280 cm⁻¹ (—C≡C—).

¹H-NMR Spectrum, 100 MHz (CDCl₃, TMS) δ in ppm: 0.8–1.2(m); 1.6–1.8(m); 4.95(s); 6.9(m); 7.25(m) in the ratio of 4:1:2:1:2.

EXAMPLE 19

Ovicidal action against Heliothis virescens and Spodoptera littoralis

Appropriate proportions of a wettable pulverulent formulation containing 25 percent by weight of the active substance to be tested were in each case diluted with specific amounts of water so that aqueous emulsions having an increasing range of concentrations were obtained. One-day-old clusters of eggs of Heliothis and Spodoptera, respectively, which had been deposited on absorbent paper, were immersed for three minutes in the respective emulsions containing the active substance, and subsequently filtered which suction on round filters. After drying of the emulsion, the clusters of eggs were placed into Petri dishes, and kept at 28° C. in darkness. The rate of emergence from the eggs compared with that of untreated control eggs was determined after 4 days. The minimum active-substance concentration necessary to effect a 100% destruction of the eggs was taken as a basis for the assessment.

Compounds according to Examples 1–18 exhibited in this test a good ovicidal action against the clusters of eggs tested.

EXAMPLE 20

Ovicidal action against Laspeyresia pomonella

Eggs of Laspeyresia pomonella deposited on filter paper were immersed for 1 minute in an acetonic aqueous solution of an active substance of each of the Examples 1–26. The eggs after drying were placed into Petri dishes and kept at 28° C. The rate of emergence from the eggs compared with that of untreated control eggs was determined after 6 days. The basis of assessment was the mortality rate with an active-substance concentration of 200 ppm.

Compounds according to Examples 1–18 exhibited in this test a good ovicidal action.

EXAMPLE 21

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray-liquor. An assessment was made after 2 and 7 days, by examination under a binocular microscope, of the living larvae and of the dead larvae, adults and eggs, and the results were expressed as percentages. The treated plants were kept during the "holding time" in greenhouse compartments at 25° C. Compounds according to Examples 1–18 exhibited a good action in the test.

What is claimed is:

1. A compound of the formula

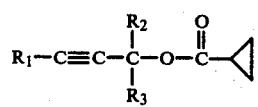

wherein $R_1$ is phenyl optionally substituted by one or more members selected from the group consisting of halogen, $C_1$–$C_5$ alkyl, $C_1$–$C_5$ alkoxy, benzyl, trifluoromethyl, hydroxyl, nitro, cyano, formyl, acetyl and $C_1$–$C_5$ alkoxycarbonyl, or thienyl, $R_2$ is hydrogen, $C_1$–$C_6$ alkyl, $C_2$–$C_6$ alkenyl, or phenyl or naphthyl optionally substituted by $C_1$ or $C_2$ alkyl, $C_1$ or $C_2$ alkoxy or halogen, and $R_3$ is hydrogen, $C_1$–$C_6$ alkyl a $C_2$–$C_6$ alkenyl.

2. A compound according to claim 1, wherein $R_1$ is phenyl optionally substituted by one or two members selected from the group consisting of halogen, $C_1$ or $C_2$ alkyl, $C_1$ or $C_2$ alkoxy, $C_1$ or $C_2$ alkoxycarbonyl, formyl, hydroxyl, nitro, cyano and trifluoromethyl, or thienyl, $R_2$ is hydrogen, $C_1$–$C_4$ alkyl, $C_2$–$C_4$ alkenyl or phenyl, and $R_3$ is hydrogen or $C_1$–$C_4$ alkyl.

3. A compound according to claim 2, wherein $R_1$ is phenyl, methylphenyl, methoxyphenyl, methoxycarbonylphenyl, chloro-, bromo- or fluorophenyl, cyanophenyl, formylphenyl, nitrophenyl, biphenyl or 1-thienyl, $R_2$ is hydrogen, methyl or vinyl, and $R_3$ is hydrogen or methyl.

4. A compound according to claim 3, wherein $R_2$ and $R_3$ are each hydrogen.

5. A compound according to claim 4, wherein $R_1$ is 4-fluorophenyl or 2-thienyl.

6. The compound according to claim 4 which is 1-(4-methoxyphenyl)-1-propyn-3-yl-cyclopropane-carboxylic acid ester.

7. The compound according to claim 5 which is 1-(4-fluorophenyl)-1-propyn-3-yl-cyclopropane-carboxylic acid ester.

8. The compound according to claim 5 which is 1-(2-thienyl)-1-propyn-3-yl-cyclopropane-carboxylic acid ester.

9. An insecticidal and acaricidal composition comprising (1) an insecticidally or acaricidally effective amount of a compound according to claim 1 and (2) a carrier.

10. A method for combatting insects and acarids which comprises applying thereto an insecticidally or acaricidally effective amount of a compound according to claim 1.

* * * * *

UNITED STATES PATENT AND TRADEMARK OFFICE
CERTIFICATE OF CORRECTION

PATENT NO. : 4,322,432
DATED : March 30, 1982
INVENTOR(S) : Achim Roloff, Et Al

It is certified that error appears in the above-identified patent and that said Letters Patent are hereby corrected as shown below:

Claim 3, column 14, line 18 reads:

1-thienyl, $R_2$ is hydrogen, methyl or vinyl, and $R_3$ is

Should read:

-- 2-thienyl, $R_2$ is hydrogen, methyl or vinyl, and $R_3$ is --

Signed and Sealed this

Twelfth Day of October 1982

[SEAL]

Attest:

GERALD J. MOSSINGHOFF

Attesting Officer     Commissioner of Patents and Trademarks